US00PP35230P2

(12) United States Plant Patent
Fang

(10) Patent No.: US PP35,230 P2
(45) Date of Patent: Jun. 20, 2023

(54) ***ONCIDIUM 21ST SCENTURY* 'HULA GIRL'**

(50) Latin Name: ***Oncidium* 21st Scentury**
Varietal Denomination: Hula Girl

(71) Applicant: James Yen Jen Fang, Mountain View, HI (US)

(72) Inventor: James Yen Jen Fang, Mountain View, HI (US)

( * ) Notice: Subject to any disclaimer, the term of this patent is extended or adjusted under 35 U.S.C. 154(b) by 0 days.

(21) Appl. No.: 17/803,810

(22) Filed: Dec. 5, 2022

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 5/02
See application file for complete search history.

*Primary Examiner* — Kent L Bell

(57) ABSTRACT

A new variety of orchid plant of the genus *Oncidium*, named *Oncidium* 21st Scentury 'Hula Girl', distinguished particularly by flowers of a clean and striking color of compact size that are highly fragrant, that are arranged pleasingly on a raceme and growing quickly to sexual maturity.

2 Drawing Sheets

Latin name of the species and grex of the plant claimed: The Latin name of the species and grex of the plant claimed is *Oncidium* 21st Scentury.

Variety denomination: The present invention comprises a new and distinct cultivar of *Oncidium* orchid and hereinafter referred to by the name *Oncidium* 21st Scentury 'Hula Girl'.

CROSS REFERENCE TO RELATED APPLICATIONS

Not Applicable.

STATEMENT REGARDING FEDERALLY SPONSORED RESEARCH OR DEVELOPMENT

Not Applicable.

BACKGROUND OF THE INVENTION

The genus *Oncidium* is one of the largest and most diverse within the orchid family; numbering more than 600 distinct species distributed throughout the American tropics and extending into South-Central America.

Many, if not most of the species within the genus, grow as epiphytes. The remaining species thrive growing as lithophytes or terrestrials. All exhibit a sympodial growth habit.

The first *Oncidium* hybrid was created in 1898 by a Mr. C. Vuylsteke and registered by the same. There are now over 7,600 unique hybrids of *Oncidium* as of June, 2022.

*Oncidium* hybridizing is accomplished through sexual methods. Asexual propagation of *Oncidium* is done in aseptic tissue culture from apical or axillary shoots.

The new cultivar was discovered within a group of sexually produced plants on May 18, 2017. The inventor selected *Oncidium* 21st Scentury 'Hula Girl' from a population of 200 plants grown in 3.25 inch square black plastic pots, grown in a poly-film covered greenhouse in Mountain View, Hi. *Oncidium* 21st Scentury 'Hula Girl' was reflowered and submitted by the inventor to a commercial tissue culture laboratory in Bangkok, Thailand on Oct. 14, 2020 for asexual reproduction via tissue culture technique.

Other seedlings of the same varieties that were used to produce *Oncidium* 21st Scentury 'Hula Girl' have been commercially available from others.

The characteristics of *Oncidium* 21st Scentury 'Hula Girl' as described herein have demonstrated to be fixed and retained through successive generations of asexual reproduction. *Oncidium* 21st Scentury 'Hula Girl' reproduces true to type. The characteristics are clearly distinguishable from the characteristics of those other plants. The inventor has reason to believe that *Oncidium* 21st Scentury 'Hula Girl' is superior to other seedlings in floriferousness, fragrance and flower color.

BRIEF SUMMARY OF THE INVENTION

The following traits have been repeatedly observed and are determined to be basic characteristics of the new cultivar which in combination distinguish this *Oncidium* orchid as a new and distinct cultivar:

Flowers of the new cultivar are burgundy, soft pink and white in color. The sepals and petals are burgundy tipped cream distally. The labellum is soft pink centrally with glossy mid-lobes, bottom third white. The callus is soft pink and develops as a swelling in the lip terminating into many small diverging horns divided by a central crest about 0.5 centimeters (cm) long. The anther cap is cream in color. The column is burgundy throughout. The column wings are rectangular and translucent. The flowers are rigid and bear an intense, pleasing fragrance.

The natural horizontal spread is 3.2 cm; natural vertical spread is 4.7 cm; dorsal sepal width 0.7 cm; dorsal sepal length 1.7 cm; petal width 0.6 cm; petal length 1.4 cm; lateral sepal width 0.6 cm; lateral sepal length 1.7 cm; labellum width 1.5 cm; labellum length 1.7 cm.

The plant produces two branching inflorescences on first bloom with 80 flowers.

Inflorescence is a basal raceme, upright or arching, branching and approximately 50 cm long. The plant is relatively compact, and the size of the inflorescence is appropriate to the overall size of the plant and typical pot size for this cultivar.

There are generally six leaves per mature psuedobulb: two from the apex and four from the base. The apical leaves measure 35 cm long and are 5 cm wide. The leaves from the base of the pseudobulb measure 10-22 cm long and are 5 cm wide. Axillary leaves, or bracts, are not common below the leaves at the base of the psuedobulb. The shape of the leaf is lanceolate acuminate, and semi-conduplicate at the base. The texture and substance is slightly undulate and somewhat coriaceous. The plants of *Oncidium* 21$^{st}$ Scentury 'Hula Girl' grow to maturity and flower in approximately 18 months.

Plants of the new cultivar have not been observed under all possible environmental conditions. The phenotype may vary significantly with variations in the environment, such as temperature, light intensity, and day length, without any change in genotype.

The instant plant differs from parent cultivars in flower color and fragrance. The closest comparison to the new cultivar can be made to the parent cultivars used to create *Oncidium* 21$^{st}$ Scentury 'Hula Girl'. The original unpatented plant material; named *Oncidium* Aka Baby and *Oncidium* Pagans Scent possess the same general growth habit and speed to maturation, but lack the uniquely colored and intensely fragrant flowers of *Oncidium* 21$^{st}$ Scentury 'Hula Girl'.

BRIEF DESCRIPTION OF THE DRAWINGS

The drawings show the colors of the new variety as nearly true as possible with an illustration of this type. In the drawings.

The drawing on the first sheet, labeled

The drawing on the second sheet, labeled

DETAILED BOTANICAL DESCRIPTION

Figure 1:
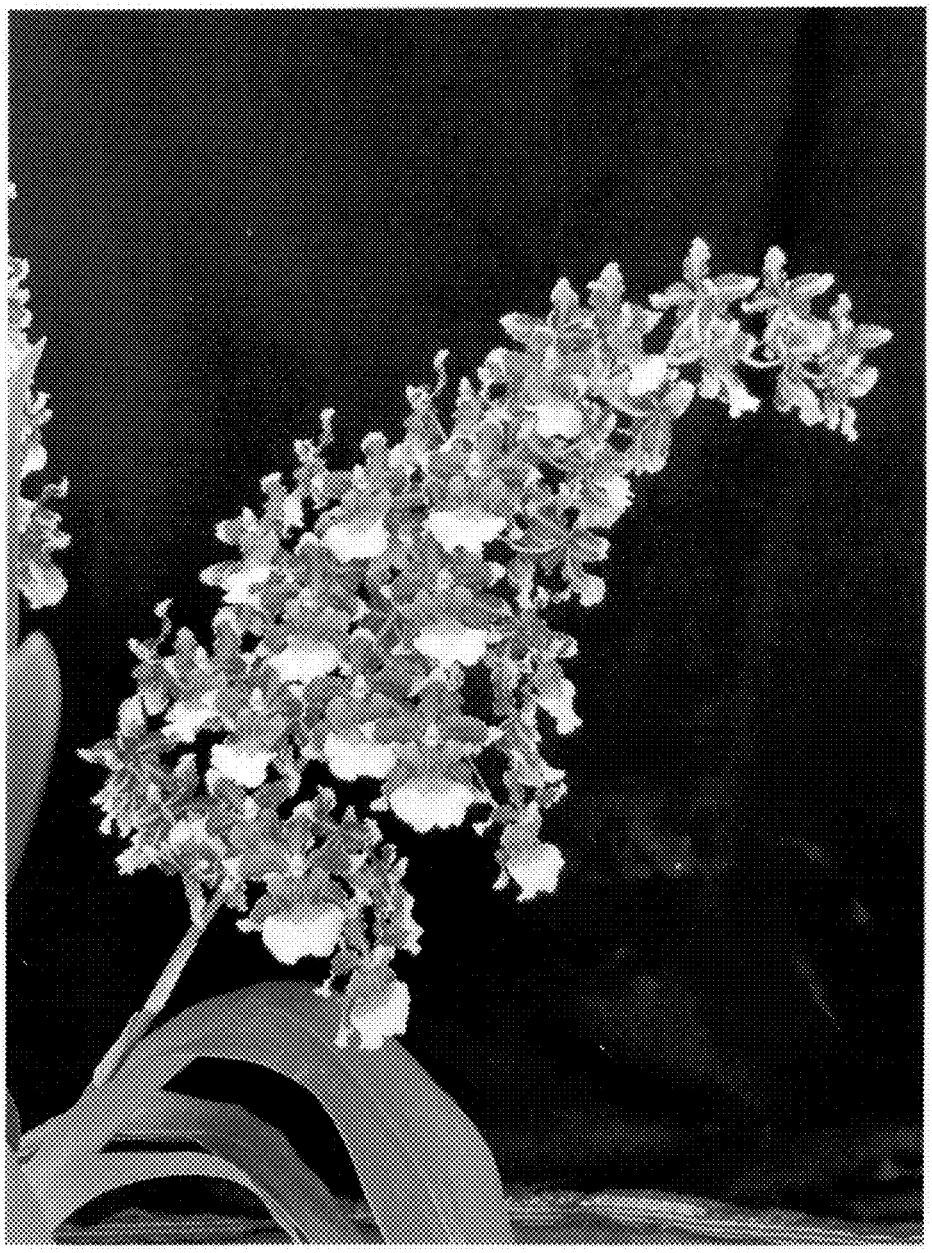
FIG. 1, is a single inflorescence of *Oncidium* 21$^{st}$ Scentury 'Hula Girl' to illustrate overall inflorescence characteristics typical of this new cultivar.
Figure 2:
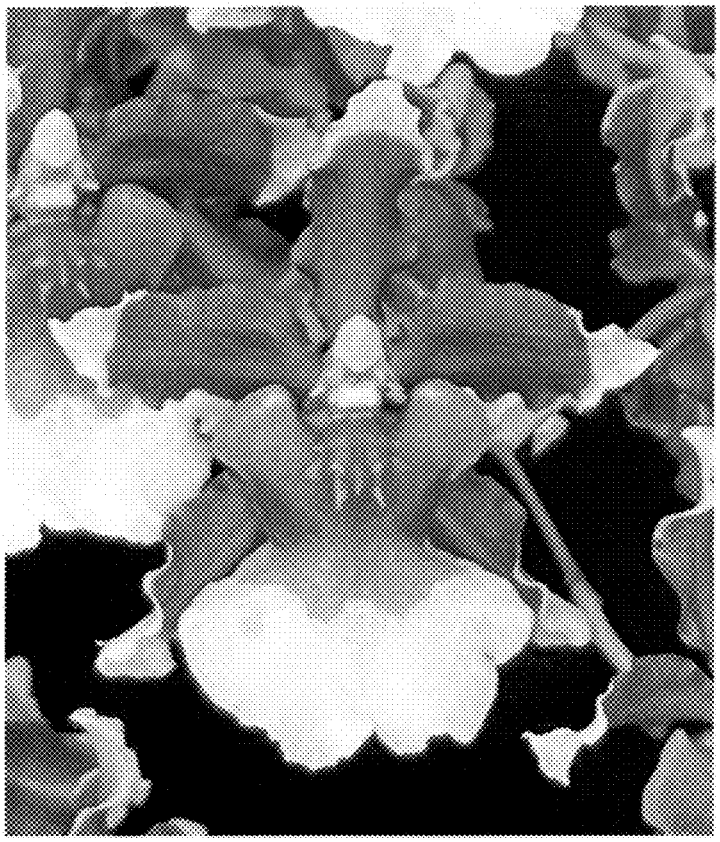
FIG. 2, is a single flower of *Oncidium* 21$^{st}$ Scentury 'Hula Girl' to illustrate shape and color.

All color references are measured against the Pantone® Color System. Colors and numerical measurements are approximate, as plant growth and development depend on environmental conditions and cultural practices such as: light levels, temperature, water quality, fertilization formula and rate, among others, without any variance in genotype.

Plants used for this description are 24 months old in vivo and grown in 3.25 inch square, black plastic pots, grown in a poly-film covered greenhouse in Mountain View, Hi.

Day temperatures range from 75-85° F. and night temperatures range from 55-65° F. Light levels are approximately 2500 foot candles. This information reflects the annual variations for the area.

Botanical classification: *Oncidium* 21$^{st}$ Scentury 'Hula Girl'.

*Parentage*.—Seedling selected from the cross of the following.

*Seed parent*.—An unnamed cultivar of *Oncidium* Aka Baby.

*Pollen parent*.—An unnamed cultivar of *Oncidium* Pagans Scent. The designations above list the Genus and grex for both parents.

Propagation:

*Type*.—Asexual propagation by aseptic tissue culture through Axillary shoot.

*Time to initiate and elongate roots in-vivo*.—Approximately 90 days.

*Time to produce fully rooted young plant*.—Approximately 250 days.

Root description: Velamen covered roots, approximately 0.2 cm in diameter, and white in color with yellow/green growing tip. The exact shades of white and yellow/green vary greatly with minimal changes to environmental conditions.

Plant description: Under optimal growing conditions, plants of the new cultivar attain a mature size of about 35 cm (top of leaf plane) and 6 cm wide (width of largest psuedobulb).

Foliage description:

*Arrangement*.—Sympodial growth habit.

*Quantity of leaves per growth*.—Each sympodial growth has shown six leaves, two on the apex of the psuedobulb and four from the axis at the base.

*Leaf length*.—Leaves measure up to 35 cm in length.

*Leaf width*.—The width of the largest leaf measures 5 cm.

*Leaf shape*.—The shape is lanceolate acuminate from base to tip, texture and substance is slightly undulate and somewhat coriaceous throughout.

*Leaf apex* (*observed*).—The apex measures approximately 35 cm.

*Psuedobulb shape*.—The psuedobulb shape is a laterally compressed ovoid.

*Psuedobulb length*.—The pseudobulb is approximately 6-10 cm long.

*Psuedobulb width*.—The pseudobulb is approximately 6 cm wide and 3 cm thick.

*Foliage color*.—Under the described growing conditions, the foliage color on both sides of the leaves is similar to Pantone® 7483C (green). There is no vein color distinction. The psuedobulb color is similar to Pantone® 378C (green).

Flower/inflorescence description:

*Description*.—Upright or arching raceme similar in color to Pantone® 378C (green) approximately 0.3-0.5 cm in diameter, coriaceous, branching, approx. 50.0 cm long on a first bloom plant with 80 flowers. Each internode is coriaceous in texture, carrying 4-6 flowers spaced 2.0-3.0 cm apart and varying between 6.0-9.0 cm in length. Buds are ovoid, 0.6-0.8 cm in diameter and 4.0-6.0 cm in length. Bud coloration is unique to each individual flower, displaying different hues as the bud matures. As such, selecting an individual color from a color chart would be both difficult and misleading. Pedicels are coriaceous in texture, approximately 0.1 cm in diameter and 0.4 cm in length. Flowers begin approximately ¼ of the way up the raceme and are spaced 2.0-3.0 cm apart. The size of the inflorescence is appropriate to the overall size of the plant and typical pot size of the cultivar.

*Dimensions*.—Flower dimensions are: natural horizontal spread is 3.2 cm; natural vertical spread is 4.7 cm; dorsal sepal width 0.7 cm; dorsal sepal length 1.7 cm; petal width 0.6 cm; petal length 1.4 cm; lateral sepal width 0.6 cm; lateral sepal length 1.7 cm; labellum width 1.5 cm; labellum length 1.7 cm.

*Coloration*.—The dominant flower color that appears on the sepals and petals is a burgundy, similar to Pantone® 188C. The sepals and petals are burgundy basally; similar to Pantone® 188C. The sepals and petals are tipped cream, similar to Pantone® 7499C. The upper two-thirds of the labellum is soft pink; similar to Pantone® 204C. The mid-lobes are soft pink; similar to Pantone® 204C. The lower third of the labellum is white; similar to Pantone® 000C. The callus is soft pink; similar to Pantone® 204C. The anther cap is cream; similar to Pantone® 7499C. The base color of the column is burgundy; similar to Pantone® 188C. The pollinia are completely concealed by the anther cap. If this is removed, the pollinia may be extracted. The pollinia are deep yellow; similar to Pantone® 143C, but range in shades of yellow as the flower ages.

Quantity of flowers & time to flower:

*Flower longevity*.—Flowers can last longer than 4 weeks on the plant with good environmental conditions. A first bloom plant will produce about 80 flowers depending on environmental conditions.

*Time to flower*.—From fully rooted tissue culture plants is approximately 18 months.

*Natural flowering season*.—This plant has appeared to be free flowering.

*Fragrance*.—An intense, sweet, pleasant fragrance is noted.

*Reproductive organs*.—The Stamens, style and stigmas are fused into a short structure called the column, possessing one terminal anther with pollen grains fused to form pollinia, which are covered by an anther cap. The stigma is located under the column behind the pollinia. The ovary is inferior, with three carpels being present.

*Column*.—The column is erect with rectangular wings on either side of the stigma, 0.1 cm wide by 0.5 cm long.

*Pollinia*.—Two oval masses of pollen are present, about 0.15 cm in diameter and 0.15 cm long.

*Stigma*.—The stigma is concave, round, very glossy and sticky.

*Ovary*.—The ovary is about 1.0 cm long by 0.2 cm wide.

*Seed*.—Seed production has not been observed.

Disease & pest resistance: Resistance or susceptibility to known pathogens and pests of *Oncidium* have not been observed on plants grown under commercial production conditions.

Hardiness zone: The type plant of *Oncidium* 21$^{st}$ Scentury 'Hula Girl' was commercially grown in Mountain View, Hi.—USDA Hardiness Zone 11. Data from other plants of *Oncidium* 21$^{st}$ Scentury 'Hula Girl' in other USDA Hardiness zones is currently unavailable.

General observations: Plants of *Oncidium* 21$^{st}$ Scentury 'Hula Girl' produce a pleasing arrangement of small sized, tri-colored, star shaped flowers with clean, striking colors on a branching raceme that is desirable in proportion for the size of the plant. The flowers are long lasting and pleasantly fragrant. The plant grows quickly to sexual maturity.

The invention claimed is:

1. A new and distinct variety of orchid plant named *Oncidium* 21$^{st}$ Scentury 'Hula Girl' substantially as illustrated and described herein.

* * * * *